United States Patent [19]

Krenzke

[11] Patent Number: 5,331,960
[45] Date of Patent: Jul. 26, 1994

[54] EVALUATION METHOD FOR EKG MAPPING

[75] Inventor: Gerhard Krenzke, Berlin, Fed. Rep. of Germany

[73] Assignee: Fehlikng Medical AG, Karlstein, Fed. Rep. of Germany

[21] Appl. No.: 984,121

[22] Filed: Dec. 4, 1992

[51] Int. Cl.[5] ............................................. A61B 5/04
[52] U.S. Cl. .................................................. 128/644
[58] Field of Search ............... 128/639, 642, 644, 695, 128/696, 699

[56] References Cited

U.S. PATENT DOCUMENTS

| 4,151,836 | 5/1979 | Arnaud et al. | 128/644 |
| 4,457,309 | 7/1984 | Elmeskog | 128/644 |
| 4,751,928 | 6/1988 | Halon et al. | 128/644 |
| 5,054,496 | 10/1991 | Wen et al. | 128/696 |

FOREIGN PATENT DOCUMENTS

| 225333A1 | 6/1984 | Fed. Rep. of Germany . | |
| 0225333 | 7/1985 | Fed. Rep. of Germany | 128/639 |

OTHER PUBLICATIONS

Kneppo et al., "Integral Characteristics of the Human Cardiac Electrical Generator from Electric Field Measurements by Means of an Automatic Cylindrical Coordinator", IEEE Transactions on Biomedical Engineering, vol. BME-26, No. 1, Jan. 1979, pp. 21-28.

"Higher Degrees Multidipolar Components Sum On the VCG Spherical Surface", *Electrocardiology 1987*, Akademie-Verlag, Berlin, 1988, Drska Z., et al., pp. 165-167.

"The Evolution of Body Surface Potential Maps Following Acute Myocardial Infarction", *Electrocardiology 1988*, Excerpta Medica, Amsterdam, 1989, Stuart W. Edwards, et al., pp. 357-360.

"Representation of Cardiac Electrical Activity By a Moving Dipole For Normal and Ectopic Beats in the Intact Dog", *Circulation Research* vol. 46, No. 3, Mar. 1980, Pierre Savard, et al., pp. 415-425.

"Body Surface Potential Mapping System Equipped, etc.", *Medical & Biological Eng. & Computing*, Great Britain, Jan. 1983, K. Yajima, et al., pp. 83-90.

"Determination of the Electrical Center of Ventricular Depolarization in the Human Heart, American Heart Journal", 1954, Ernest Frank, Ph.D., pp. 670-692.

"Problems of Three-Dimensional Vectorcardiography", Int. Coll., Stary Smokovec, 1961, Publishing House of the Slovakian Academy of Sciences, Bratislava, 1963, pp. 43-54.

"An Accurate, Clinically Practical System For Spatial Vectorcardiography", Ernest Frank, Ph.D., *Circulation*, vol. XIII, May 1956, pp. 737-749.

(List continued on next page.)

Primary Examiner—Lee S. Cohen
Assistant Examiner—Jeffrey R. Jastrzab
Attorney, Agent, or Firm—Irvin A. Lavine

[57] ABSTRACT

The invention relates to EKG mapping with a plurality of electrodes attachable to the thorax of a patient at known distance from the heart, wherein time-dependent parameters that specially accentuate the multipole components of the cardiac electrical field are calculated from the voltages at the electrodes. The mapping takes place using the following steps:

calculating the voltages projected onto a sphere, the center of which coincides with the electrical center of the heart, from the electrode voltages using the measured electrode distances from the electrical center of the heart, correcting the projected voltages using correction factors for the influence of the conductivity structure in the thorax and the movement of the electrical center of the heart, converting the corrected voltages into a parameter, the values of which are assumed to be constant over the spherical surface, assuming a dipole field, calculating the differences between this parameter and the mean value over the spherical surface, and representing these differences as isointensity lines on a sphere.

3 Claims, 5 Drawing Sheets

OTHER PUBLICATIONS

"Use of the Finite Element Method to Determine Epicardial From Body Surface Potentials Under A Realistic Torso Model", Y. Yamashita, et al. *IEEE Transactions on Biomedical Engineering*, vol. BME-31, No. 9, Sep. 1984, pp. 611–621.

"The Depolarization Sequence of the Human Heart Surface Computed From Measured Body Surface Potentials", G. Huiskamp, et al., *IEEE Transactions on Biomedical Engineering*, vol. 35, No. 12, Dec. 1988, pp. 1047–1058.

"Model Studies With the Inversely Calculated Isochrones of Ventricular Depolarization", Jan J. M. Cuppen, *IEEE Transactions on Biomedical Engineering*, vol. BME-31, No. 10, Oct. 1984, pp. 652–659.

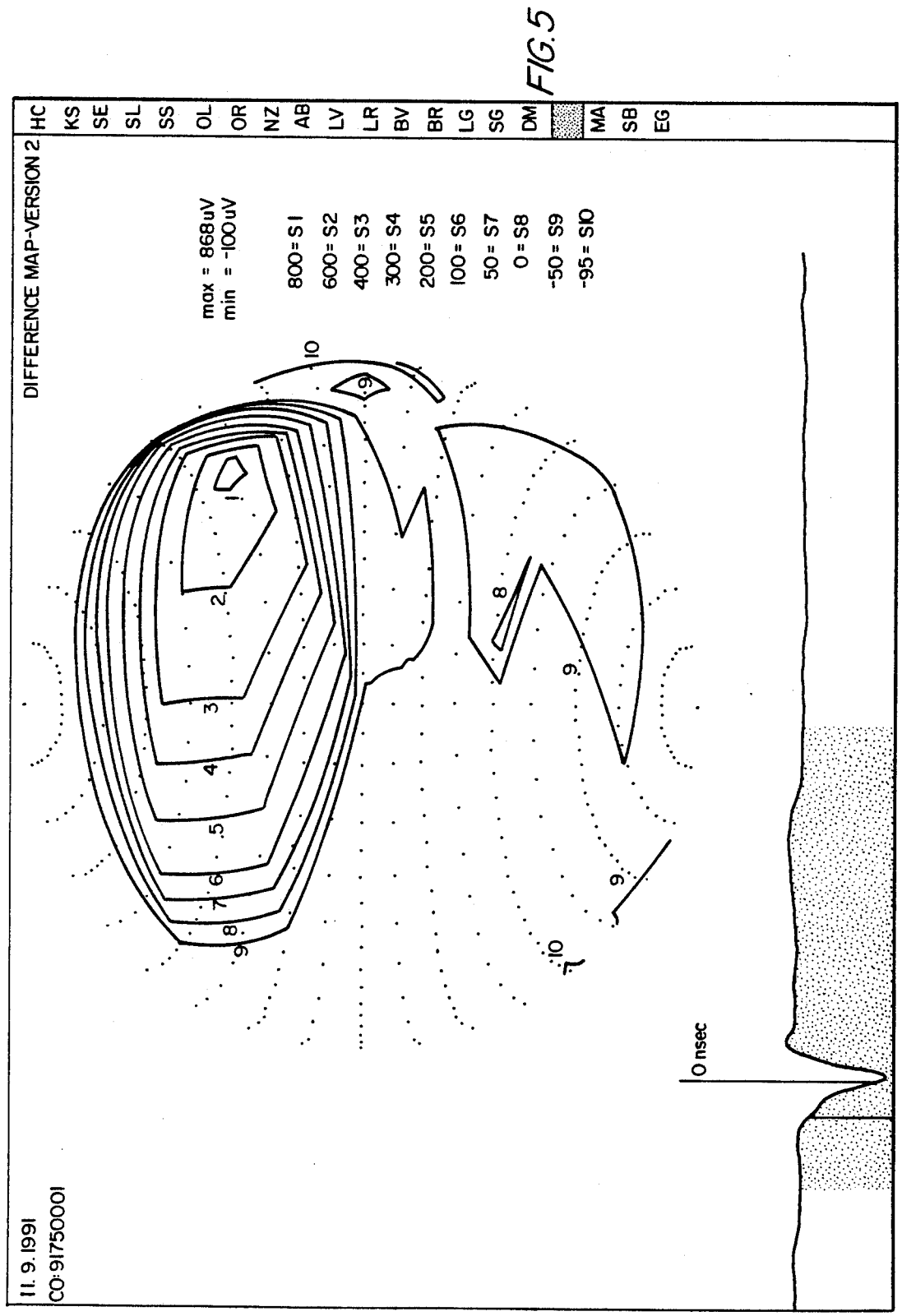

EVALUATION METHOD FOR EKG MAPPING

BACKGROUND OF THE INVENTION

The invention relates to an evaluation method for ECG mapping, in which a plurality of electrodes attachable to the thorax of the patient at known distance from the heart are used, and in which time-dependent parameters that specially accentuate the multipole components of the cardiac electrical field are calculated from the voltages at the electrodes.

In cardiological diagnostics, a technique known as ECG mapping, in which a plurality of electrodes for detecting cardiac potentials are disposed on the thoracic surface, is used to represent cardiac potentials. In this technique, it is known how to represent the cardiac potentials recorded with the electrodes on the thoracic surface imagined to be unrolled as a flat figure (H. Abel: Electrocardiology 19888, Excerpta Medica, Amsterdam, pp. 357–360). This technique has the disadvantage that it fails to consider the different distances of the lead electrodes from the electrical center of the heart and the influence thereof on the electrical field.

In order to consider the influence of thoracic configuration on the potential field measured at the thoracic surface, the potential field at the cardiac surface is calculated from that potential field. Such methods are known as solutions of the "inverse problem". Either a model surface of the heart is assumed (IEEE Transactions on Biomedical Engineering, Vol. 31 (1984), No. 9, pp. 611–621) or the shape of the heart can be determined by means of NMR tomography (NMR=nuclear magnetic resonance).

Instead of representing the potential field as an intensity field, isochrones on the cardiac surface are also plotted both for model hearts (IEEE Transactions on Biomedical Engineering, Vol. 31 (1984), No. 10, pp. 652–659) and for heart shapes measured by tomography (IEEE Transactions on Biomedical Engineering, Vol. 35 (1988), No. 12, pp. 1047–1058).

The calculation of the potential distribution or of isochrones on the surface of a theoretical heart shape can lead to considerable misinterpretations, if the shape and position of the model heart differ from those of the actual heart. This method is suitable only for theoretical studies. Measurement of the actual heart shape by NMR tomography can be life-threatening for patients with metallic implants, such as pacemaker patients and heart-transplant patients with IMEK electrodes. The actual shape and position of the heart cannot be determined in this way in such patients. In other patient groups, considerable difficulties occur routinely in coupling the image transmission from the tomograph to the ECG mapping apparatus.

A known proposal is to project the ECG curves measured on the thorax onto a sphere around the electrical center of the heart ("Problems of three-dimensional vectorcardiography", Int. Coll. Stary Smokovec, 1961. Publishing House of the Slovakian Academy of Sciences, Bratislava, 1963, pp. 43–54). The projection is made along the lead lines from sphere center to electrode corresponding to the dipole hypothesis. The diagrammatic representation of complete ECG curves at the projection points on the spherical surface is unclear, has poor resolution in time and amplitude and does not contain data reduction for compressed information, and so is unsuitable for routine diagnosis.

Furthermore, the representation of ECG curves, equipotential lines or isochrones as in the method described in the foregoing is not suitable, regardless of the representation surface, for specially marking perturbation boundaries of local perturbations of field propagation, because local amplitudes must always be assessed as a proportion of the total state of excitation. At the measuring point under the electrode, the potential is always a summation potential produced by all excited locations in the heart. Locally confined perturbations, which are represented in particular in the higher multipole components, are therefore suppressed.

In order specially to represent the higher multipole components, a proposal is known (Electrocardiology '87, AkademieVerlag Berlin 1988, pp. 165–167) according to which the voltages of Frank's voltage vector projected to an electrode location are subtracted from the voltage measured thereat. The projection of Frank's voltage vector is undertaken using a transformation matrix, which was obtained statistically from comparisons of ECG curves. A falsifying effect is introduced by the fact that the same matrix is used regardless of the thoracic configuration of the subjects. Since the thoracic shape also is considered neither individually nor as a mean for the measured voltage, the difference between the measured voltage and the projection of Frank's voltage vector is also not constant for a dipole field, and the effect of higher multipoles is superposed on the influence of thoracic configuration, thus leading to severe distortions of the isopotential lines and making comparisons between patients difficult.

SUMMARY OF THE INVENTION

The method according to the invention includes the following steps:
- calculating the voltages projected onto a sphere, the center of which coincides with the electrical center of the heart, from the electrode voltages by means of the measured electrode distances from the electrical center of the heart, and
- correcting the projected voltages with correction factors for the influence of the conductivity structure in the thorax and the movement of the electrical center of the heart,
- converting these corrected voltages into parameters, the values of which are constant over the spherical surface, assuming a dipole field, and
- calculating the differences between these parameters and the mean value over the spherical surface and representing them as isointensity lines on a sphere.

The object of the present invention is to provide a method of EKG mapping to enable the plotting of a representation, by isointensity lines on a sphere, of a normalized representation of the extent and position of local field distributions and the propagation of the cardiac electrical field, without knowing exactly the shape and position of a heart, and without distortion or falsification due to the thoracic configuration.

BRIEF DESCRIPTION OF THE DRAWINGS

The method according to the invention will be explained hereinafter by means of practical examples, by referring to the following drawings wherein:

FIG. 5 shows the isointensity line diagram of difference map II in the case of an aneurism.

DESCRIPTION OF THE PREFERRED EMBODIMENTS

Figure 1:
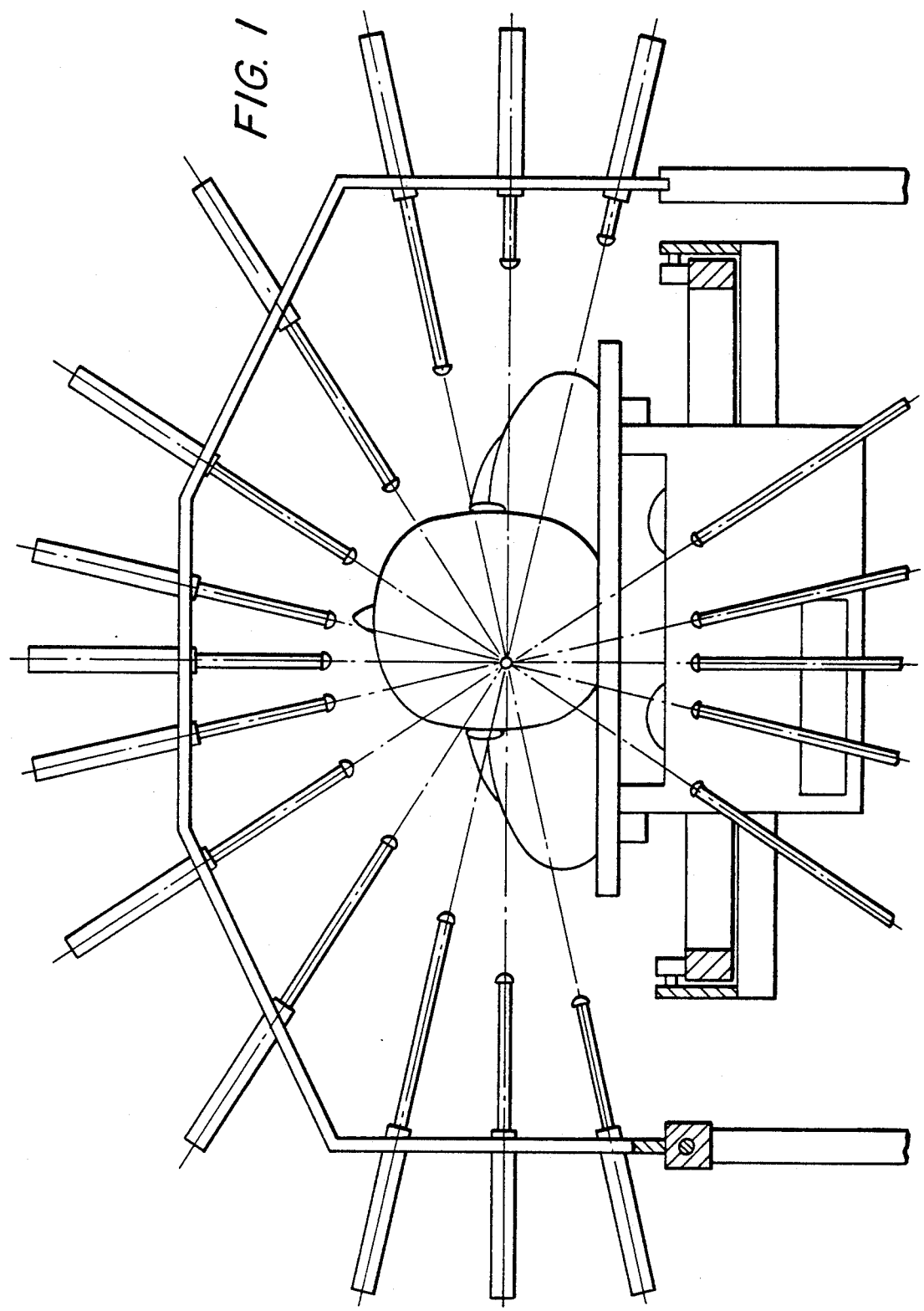
FIG. 1 shows a section through a lead system, together with the schematic arrangement of the electrodes.

In the first step, voltages are measured at a plurality of points on the thorax of the patient against an electrical reference point, e.g., the "central terminal" according to Wilson, using a device of the type shown schematically in section in FIG. 1, e.g., per East German Patent 225 333 A1. In addition, the distance from the electrodes at the measuring points to the electrical center of the heart is determined, the electrical center of the heart being brought into coincidence with a system reference point, after the position of the electrical center of the heart in the thorax of the patient has been determined in known manner (Circulation XIII (1956), No. 5, pp. 737-349).

From the voltage $U_m$ measured on the thorax at an electrode at the distance $r_m$ from the center of the heart, there is obtained the corrected voltage projected onto a sphere with radius $r_k$, expediently set equal to 10 cm, around the center of the heart as the center of the sphere:

$$K_m = a_m \frac{r_m^2 U_m}{r_k^2} \quad (1)$$

Figure 2B:
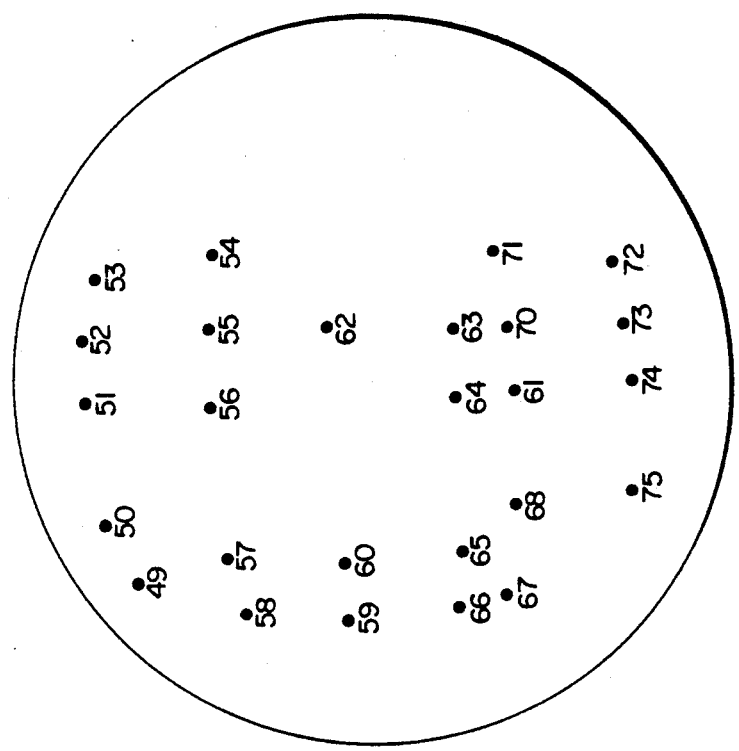
FIGS. 2A and 2B show the projection sphere with the projected electrode points, ventral side and dorsal side.
Figure 2A:
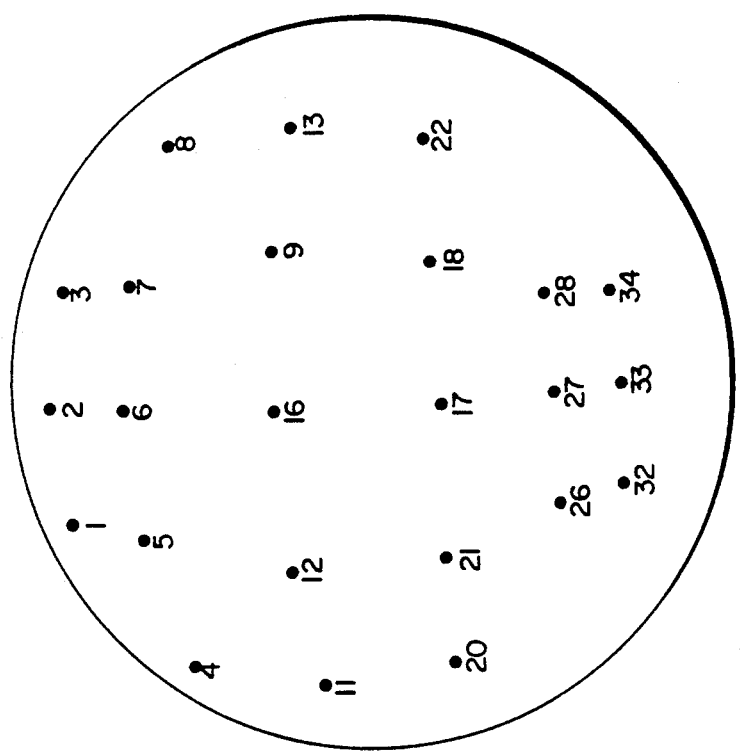

The projection points for a lead system according to FIG. 1 are illustrated in FIG. 2 on the ventral and dorsal sides of the projection sphere. $a_m$ is an empirically determined correction factor.

Equation (1) is obtained from the dipole model. As regards "mirror studies" to determine the electrical center of the heart, it is known (American Heart Journal, Vol. 49 (1955), pp. 670-681) that what is found is not a point but instead a solid in which this point must be defined. In the "mirror studies", the entire QRS complex is usually compared for congruent curve form at the mirrorimage lead points. If the voltages are considered at specified instants, it is seen (Circulation Research, Vol. 46 (1980), pp. 415-425) that the dipole position also moves. The movement of the dipole position is one of the reasons for the extent of the describing solid of the dipole position. Another reason is the conductivity inhomogeneity of the medium surrounding the heart. These factors that influence the dipole field can be compensated with the correction factor $a_m$. The correction factors at the electrode positions are chosen such that, for subjects with healthy hearts, the corrected field distribution on the spherical surface corresponds on average to a dipole field. During the QRS complex, the position and magnitude of the maximum and minimum amplitudes on the spherical surface are determined every 2 ms. The minimum values are adjusted with a correction factor that makes the product equal to the maximum value. By interpolating between these measured points representing the position and magnitude of the correction factor, closed spatial curves are obtained on the spherical surface, along which curves the correction factor continuously changes. Two electrode projection points on the sphere are now connected with a great circle. The great circles between the electrode projection points are intersected by a different number of spatial curves in different subjects. The correction factors of the spatial curves at the intersections have different magnitudes. The extrapolated correction factors at the electrode positions are determined by means of linear regression of these intersection correction factors. If the correction factors at one electrode position are different in connection with adjacent electrode positions, the average is taken. Adjacent electrode positions are now obtained between which their great circles are not intersected by any spatial curve. The mean value of the correction factors of the two most closely spaced electrode positions having correction factors is assigned to these electrode positions.

To calculate difference map I, it is now assumed that a measured parameter exists for the dipole field, i.e., Frank's EKG. Frank's EKG can be taken as an approximate measure of the dipole field because the interconnection of a plurality of electrodes by the Frank network brings about a certain averaging effect, which suppresses smaller perturbations of the electric field, as is also known from tests (H. Semmler: The clinical merit of the corrected orthogonal resting EKG according to Frank in comparison with the conventional resting electrocardiogram for detection of coronary atherosclerosis. Dissertation B, Humboldt University, Berlin, 1979).

Frank's voltage vector $F_m$ is determined from the three leads X, Y, Z of Frank's EKG, which is recorded together with the mapping leads. The projection of the voltage vector onto the lead axis from the center of the sphere to the m-th electrode with coordinates $R_m$, $S_m$, $T_m$ yields $$F_m = \frac{X R_m + Y S_m + Z T_m}{\sqrt{R_m^2 + S_m^2 + T_m^2}} \quad (2)$$

These projections of the voltage vector correspond to measured values on a spherical surface with the unknown radius $r_y$. This radius results because the values of lead Y are not corrected in the Frank system, i.e., $r_y$ corresponds approximately to the distance from the center of the heart to the left groin. The projected voltages of the Frank system relate to the corrected electrode voltages in the ratio of $r_k^2/r_y^2$. The difference $D_m$ of the two voltages $$D_m = K_m - F_m \quad (3)$$

This difference $D_m$ would therefore have to be constant over the entire spherical surface. In order to be able to observe even small perturbations, the differences $D_m$ are averaged for all electrodes as follows.

$$M = \frac{1}{n} \sum_{\mu=1}^{n} A_\mu D_\mu \quad (4)$$

M is the average of the voltage differences $D_m$.

Figure 3:
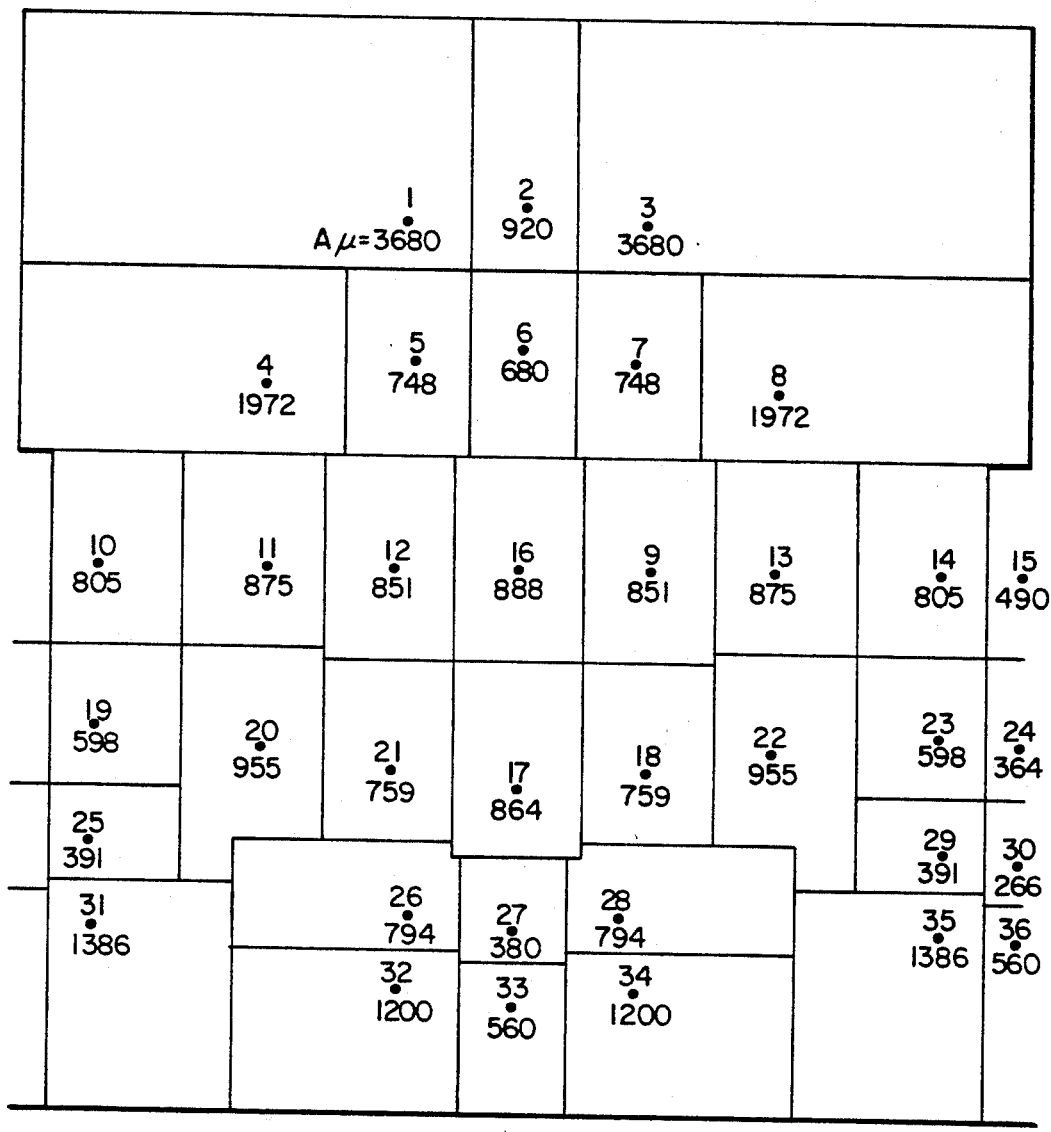
FIG. 3 shows how the areas allocated to the electrodes on the ventral side of the sphere are apportioned.

$A_\mu$ is a correcting area element on the spherical surface. The particular $\mu$-th electrode is then located in defined manner inside the associated correcting area element $A_\mu$. FIG. 3 shows the arrangement of correcting area elements for the ventral hemisphere of FIG. 2. The rectangles are constructed such that the electrode points in neighboring rectangles are approximately equidistant from the line separating these two rectangles. The total of all correcting area elements yields the area content of the entire projection surface, i.e., of the sphere. $A_M$ is the mean value of all area elements $A_\mu$. The differences $Z_m$ for all n electrodes are determined by:

$$Z_m = |MN - A_M D_m| \quad (5)$$

The values $Z_m$ are ordered by magnitude and the p values of $D_m$ (e.g., p=5) belonging to the p largest values of $Z_m$ are excluded from the calculation of a corrected mean value $M_K$ by:

$$M_k = \frac{1}{n-p} \sum_{\mu=p+1}^{n} A_\mu D_\mu \quad (6)$$

Figure 4:
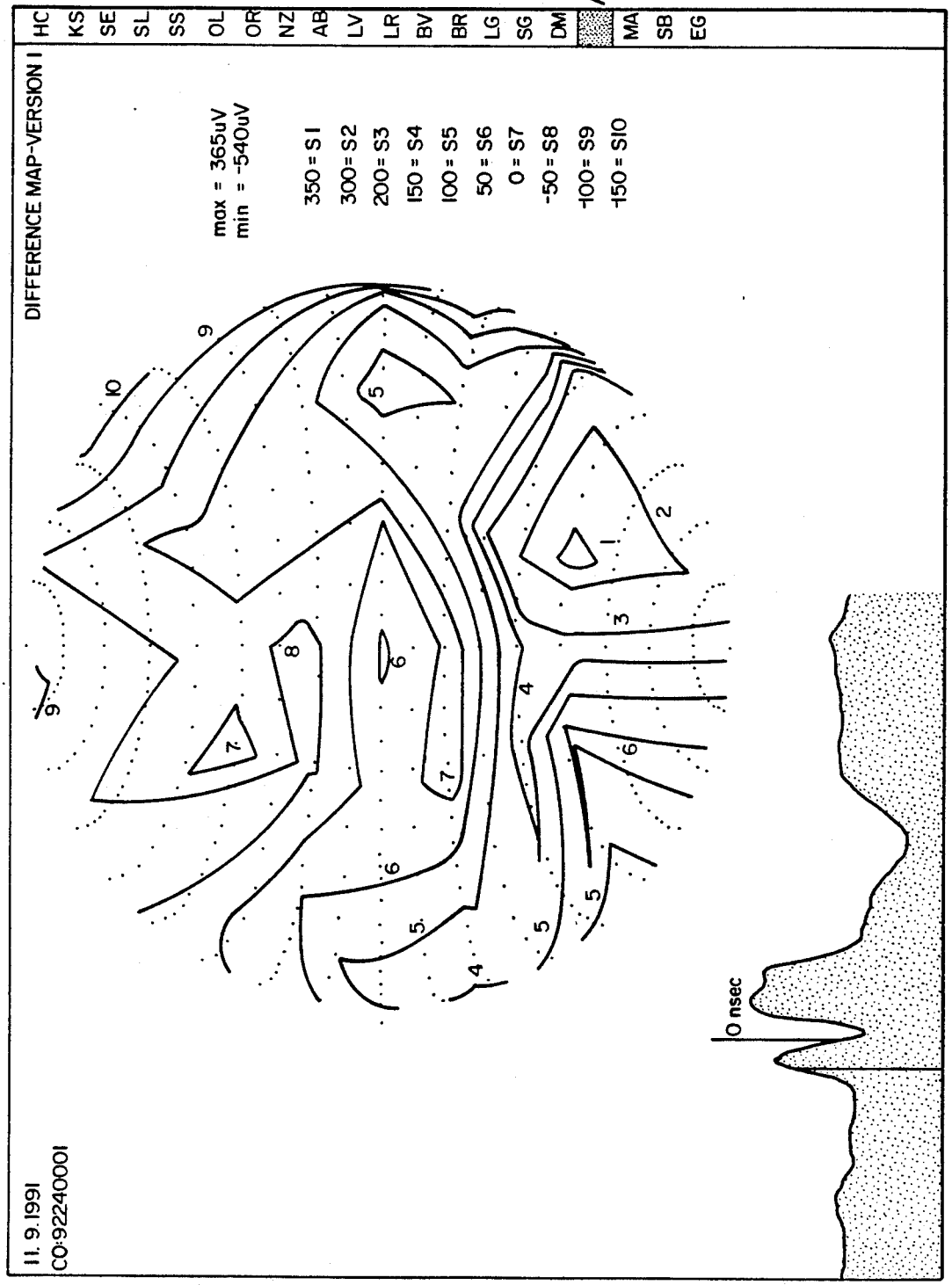
FIG. 4 shows the isointensity line diagram of difference map I in the case of heart rejection after heart-transplant operation.

Difference map I is obtained by plotting the corrected differences $$W_m = M_k - A_M D_m \quad (7)$$

as isointensity lines. The diagram (see FIG. 4) is generated for a selected instant during the EKG cycle. The isointensity lines of successive instants are presented so rapidly that the movement of these lines on the spherical surface takes place at a tempo that can be followed by the eye and that is time-delayed relative to the normal excitation sequence. In FIG. 4, the sphere around the electrical center of the heart is represented in frontal view. The lower half of the figure shows one of the 75 EKG derivatives used for calculating the difference map at the marked instant. At that instant, the normal excitation of the right ventricle is missing. This ischemia criterion is a clear sign that the rejection reaction is present in a heart-transplant patient.

Another parameter derived from the electrical field of the heart is graphically illustrated in the form of isointensity lines in difference map II, FIG. 5. In this difference map II, a normalized difference is calculated for each electrode m from the corrected voltage amplitude by means of the equation $$D_m = \frac{A_M \left|\frac{K_m}{\cos \alpha_m}\right| - \frac{1}{n} \sum_{\mu=1}^{n} A_\mu \left|\frac{K_\mu}{\cos \alpha_\mu}\right|}{\frac{1}{n} \sum_{\mu=1}^{n} A_\mu \left|\frac{K_\mu}{\cos \alpha_\mu}\right|} \quad (8)$$

The angle $\alpha_\mu$ can then be calculated from the three measured leads X, Y, Z of Frank's EKG and from the components of the position vector R, S, T of the $\mu$-th electrode by means of the equation $$\cos \alpha_\mu = \frac{X R_\mu + Y S_\mu + Z T_\mu}{\sqrt{R_\mu^2 + S_\mu^2 + T_\mu^2} \sqrt{X^2 + Y^2 + Z^2}} \quad (9)$$

The parameters in equation (8) that are constant over the spherical surface under ideal conditions are $K_m/\cos \alpha_m$ and $K_\mu/\cos \alpha_\mu$.

Difference map II can be regarded as a measure of how much the conductivity in the solid angle subtended by the area elements belonging to the electrode deviates from the mean conductivity, which is assumed to be homogeneously distributed. It is suitable in particular for representing boundaries of the extent of areas with conductivity perturbation, e.g., during infarction or aneurism, as shown in FIG. 5. The sphere around the electrical center of the heart is rotated 90 degrees to the left away from the observer, who is therefore looking toward the left lateral wall of the heart. The clearly bounded region of the aneurism extends forward around the high-lying posterolateral infarction.

List of output parameters and calculated parameters.

$U_m$, $U_\mu$ = voltage at electrode m or $\mu$ $a_m$, $a_\mu$ = correction factor for the voltage at electrode m or $\mu$ X, Y, Z = coordinates of Frank's vector $R_m$, $S_m$, $T_m$ = coordinates of electrode m $R_\mu$, $S_\mu$, $T_\mu$ = coordinates of electrode $\mu$ $A_\mu$ = area element of a spherical surface $A_M$ = mean value of all area elements of a spherical surface $r_m$, $r_\mu$ = distance of electrode m or $\mu$ from the electrical center of the heart $r_k$ = radius of a projection sphere $r_y$ = radius of the projection sphere of Frank's lead system $\cos \alpha_m$, $\cos \alpha_\mu$ = angle between lead axis at electrode m or $\mu$ and Frank's vector $K_m$ = voltage at electrode m, projected onto a sphere and corrected $F_m$ = projection of Frank's voltage vector onto the lead axis of the m-th electrode $D_m$ = voltage difference M = mean value of voltage differences $Z_m$ = mean-value deviation of a voltage difference $M_k$ = corrected mean value of voltage differences $W_m$ = difference map I $D_m$ = difference map II

I claim:

1. A method for EKG mapping comprising:
   (a) measuring, by a plurality of electrodes m at the thorax of a patient at known distances from the center of the heart of the patient, voltages produced by the heart;
   (b) calculating, from the measured voltages and the distances from the electrodes to the electrical center of the heart, voltages projected onto the surface of a sphere, the center of which coincides with the electrical center of the heart;
   (c) correcting the projected voltages with a correction factor including factors for influence of the conductivity inhomogeneity of medium surrounding the heart and change in location of the electrical center of the heart to obtain corrected voltages;
   (d) converting the corrected voltages into parameters, the values of which are assumed to be constant over the surface of the sphere, assuming a dipole field;
   (e) calculating the mean value of said parameters;
   (f) calculating differences between the parameters and the mean value of said parameters over the spherical surface; and
   (g) plotting said differences as isointensity lines on a sphere.

2. A method according to claim 1, wherein each parameter at each said electrode m, which parameter is assumed to be constant over the spherical surface of a sphere with radius $r_k$, is obtained by calculating a voltage difference $D_m$ according to the formula $$D_m = a_m \frac{U_m r_m^2}{r_k^2} - F_m$$

where:
- $D_m$ is the difference in voltages,
- $U_m$ is the projected voltage measured at each said electrode m,
- $F_m$ is the projection of a voltage vector calculated from Frank's EKG onto the lead axis defined by the electrical center of the heart and the position of each said electrode m,
- $r_m$ is the distance between each said electrode m and the electrical center of the heart,
- $a_m$ is an empirically determined correction factor for influence of the conductivity inhomogeneity of medium surrounding the heart, and change in location of the electrical center of the heart, the calculating of differences derived from the parameters is in accordance with the formula $$W_m = \left[ \frac{1}{n-p} \sum_{\mu=p+1}^{n} A_\mu D_\mu \right] - A_M D_m$$

where
- $D_m$, $D_\mu$ is the voltage difference at each said electrode m respectively $\mu$;
- $A_\mu$ is a weighting area element on the surface of the sphere which takes into consideration different mutual distances of the electrodes from each other,
- $A_M$ is the mean value of all $A_\mu$, and wherein
p values of $D_\mu$ are not used for the calculation of $W_m$; that belong to the p largest values of differences are calculated according to the formula $$Z_m = \left| \left[ \frac{1}{n} \sum_{\mu=1}^{n} A_\mu D_\mu \right] - A_M D_m \right|$$

where $Z_m$ defines the p values of $D_m$.

3. A method according to claim 1, wherein the parameter for each said electrode m assumed to be constant on the spherical surface of a sphere with radius $r_k$ is $$\frac{a_m r_m^2 U_m}{r_k^2 \cos \alpha_m} \text{ or } \frac{a_\mu r_\mu^2 U_\mu}{r_k^2 \cos \alpha_\mu}$$

for the m-th and $\mu$-th electrode, respectively, the steps of calculating the parameters to obtain normalized difference $D_m$ according to the formula $$D_m = \frac{A_M \left| \frac{a_m r_m^2 U_m}{\cos \alpha_m} \right| - \frac{1}{n} \sum_{\mu=1}^{n} A_\mu \left| \frac{a_\mu r_\mu^2 U_\mu}{\cos \alpha_\mu} \right|}{\frac{1}{n} \sum_{\mu=1}^{n} A_\mu \left| \frac{a_\mu r_\mu^2 U_\mu}{\cos \alpha_\mu} \right|}$$

said plotting of isointensity lines being of said differences,
where $U_m$ and $U_\mu$ are the voltage amplitudes at the m-th and $\mu$-th electrodes,
$\alpha_m$ and $\alpha_\mu$ are the angles between the lead axis of the m-th and $\mu$-th electrodes and Frank's voltage vector calculated from Frank's EKG projected onto the lead axis calculated from Frank's EKG projected onto the lead axis defined by the electrical center of the heart and the position of the m-th and $\mu$-th electrode,
$A_\mu$ is a weighting area element on the projection surface for different mutual distances of the electrodes from each other,
$A_M$ is the mean value of all $A_\mu$,
$r_m$ and $r_\mu$ are the distances of the m-th and $\mu$-th electrodes from the electrical center of the heart,
$a_m$ and $a_\mu$ are empirically determined correction factors for influence of the conductivity inhomogeneity of medium surrounding the heart and change in location of the electrical center of the heart, and
calculating $\cos \alpha_m$ and $\cos \alpha_\mu$ from the formula $$\cos \alpha_\mu = \frac{X R_\mu + Y S_\mu + Z T_\mu}{\sqrt{R_\mu^2 + S_\mu^2 + T_\mu^2} \sqrt{X^2 + Y^2 + Z^2}}$$

wherein the coordinates $\{R_\mu, S_\mu, T_\mu\}$ of the $\mu$-th electrode and the components $\{X, Y, Z\}$ of the voltage vector are measured in accordance with Frank's lead system.

* * * * *